US009420979B2

(12) United States Patent
Pettinato et al.

(10) Patent No.: US 9,420,979 B2
(45) Date of Patent: Aug. 23, 2016

(54) SYSTEM SUBJECT SUPPORT ACCESSORY

(75) Inventors: Jeremy David Pettinato, Mentor, OH (US); Rosemarie Sheridan, Mayfield Village, OH (US); Samuel Andreas Johansson, Cleveland Heights, OH (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 193 days.

(21) Appl. No.: 14/116,514

(22) PCT Filed: May 14, 2012

(86) PCT No.: PCT/IB2012/052394
§ 371 (c)(1),
(2), (4) Date: Nov. 8, 2013

(87) PCT Pub. No.: WO2012/156895
PCT Pub. Date: Nov. 22, 2012

(65) Prior Publication Data
US 2014/0083436 A1    Mar. 27, 2014

Related U.S. Application Data

(60) Provisional application No. 61/486,789, filed on May 17, 2011.

(51) Int. Cl.
*A61B 6/04* (2006.01)
*A61B 6/10* (2006.01)
(Continued)

(52) U.S. Cl.
CPC ............. *A61B 6/0428* (2013.01); *A61B 5/0555* (2013.01); *A61B 5/704* (2013.01);
(Continued)

(58) Field of Classification Search
CPC ...... A61B 6/0421; A61B 6/0428; A61B 6/04; A61B 5/704; A61B 5/0555; A61B 6/03; A61B 6/032; A61B 6/037; A47D 7/00; A47D 9/00; A61G 2200/50; A61G 13/101; A61G 13/12; A61G 13/1225; A61G 13/128; A61G 13/1295; A61F 5/3769
USPC ........... 292/3, 44, 24, 25, 31, 54, 95, 129, 99, 292/216, 229, 198, 332, 333, 336
See application file for complete search history.

(56) References Cited

U.S. PATENT DOCUMENTS 3,040,174 A * 6/1962 Robin ........................... 378/174
3,215,834 A * 11/1965 Tayman ...................... 378/174
(Continued)

FOREIGN PATENT DOCUMENTS

CN    2395691 Y    9/2000
FR    2523433      9/1983
(Continued)

*Primary Examiner* — Nicholas Polito
*Assistant Examiner* — David R Hare (57) ABSTRACT

A subject support accessory (126, 200) includes a securing mechanism (300) configured to secure to a tabletop of the subject support anywhere along a long axis of the tabletop by lowering the securing mechanism onto the tabletop. A method of securing a subject support accessory (126, 200) to a subject support (116) of an imaging system (100) includes receiving, via slots (316, 318) in pivoting arms (304, 310) of the accessory, the tabletop, wherein the accessory is vertically lowered onto the subject support and the slots physically engage the tabletop, and releasably locking the arms, in response to receiving a force, so that the arms no longer pivot, thereby securing the subject support accessory to the subject support.

18 Claims, 6 Drawing Sheets

(51) Int. Cl.
   *A61B 5/00*    (2006.01)
   *A61G 13/10*   (2006.01)
   *A61B 5/055*   (2006.01)
   *A61B 6/03*    (2006.01)

(52) U.S. Cl.
   CPC ............... *A61B 6/032* (2013.01); *A61B 6/037* (2013.01); *A61G 13/101* (2013.01); *A61B 6/03* (2013.01); *A61B 6/0421* (2013.01)

(56) References Cited

U.S. PATENT DOCUMENTS

| | | | |
|---|---|---|---|
| 3,840,221 A * | 10/1974 | Hogan | A61B 6/04 108/143 |
| 3,984,093 A | 10/1976 | Pretlow, III | |
| 4,045,678 A * | 8/1977 | Rickard | 378/174 |
| 4,137,456 A * | 1/1979 | Hogan | 378/208 |
| 4,277,218 A * | 7/1981 | Schweichler | A61G 7/1019 296/20 |
| 5,329,934 A * | 7/1994 | Bowman | 5/603 |
| 5,475,884 A * | 12/1995 | Kirmse | A61B 6/04 378/209 |
| 5,611,638 A * | 3/1997 | Dorr | A61G 7/1019 403/321 |
| 5,735,002 A * | 4/1998 | Kistner | A61G 7/103 5/81.1 HS |
| 5,983,426 A | 11/1999 | Vanek et al. | |
| 6,470,520 B1 * | 10/2002 | Weismiller | A61G 13/0009 5/602 |
| 6,618,613 B1 * | 9/2003 | Shukla et al. | 600/425 |
| 6,865,411 B2 * | 3/2005 | Erbel | A61B 6/0421 600/407 |
| 7,261,264 B2 * | 8/2007 | Moran | A01K 1/0356 24/573.11 |
| 7,736,056 B2 | 6/2010 | Tybinkowski et al. | |
| 8,763,177 B2 * | 7/2014 | Shah et al. | 5/603 |
| 8,898,837 B2 * | 12/2014 | Iizuka | A61B 5/055 5/600 |
| 2005/0005356 A1 * | 1/2005 | Zacharopoulos | A61B 6/04 5/601 |
| 2006/0293589 A1 * | 12/2006 | Calderon et al. | 600/415 |
| 2007/0050908 A1 * | 3/2007 | Kogan et al. | 5/128 |
| 2009/0217456 A1 * | 9/2009 | Lempen | A61G 1/0293 5/601 |
| 2011/0099720 A1 * | 5/2011 | Wyslucha et al. | 5/658 |
| 2011/0145991 A1 * | 6/2011 | Bridge | A61B 6/04 5/601 |

FOREIGN PATENT DOCUMENTS

| | | |
|---|---|---|
| FR | 2591883 A1 | 6/1987 |
| WO | 02094100 A1 | 11/2002 |

* cited by examiner

SYSTEM SUBJECT SUPPORT ACCESSORY

CROSS REFERENCE TO RELATED APPLICATIONS

This application is a national filing of PCT application Ser. No. PCT/IB2012/052394, filed May 14, 2012, published as WO 2012/156895 A1 on Nov. 22, 2012, which claims the benefit of U.S. provisional application Ser. No. 61/486,789 filed May 17, 2011, which is incorporated herein by reference.

FIELD OF THE INVENTION

The following generally relates to an imaging system subject support accessory and is described with particular application to computed tomography (CT). However, the following is also amenable to other imaging modalities.

BACKGROUND OF THE INVENTION

A computed tomography (CT) scanner includes a rotating gantry rotatably supported by a stationary gantry. The rotating gantry supports an x-ray tube, which emits radiation that traverses an examination region and a patient therein, and a detector array that detects radiation traversing the examination region and generates projection data indicative of the detected radiation. A reconstructor reconstructs the projection data and generates volumetric image data indicative of the portion of the patient in the examination region. A subject support supports the patient in the examination region before, during and/or after scanning. Generally, the subject support includes a base, which is affixed to the floor of the examination room and is configured to move vertically and a tabletop, which is affixed to the base and is configured to translate horizontally.

With an adult, the patient lies on the tabletop, and the tabletop moves the patient in and out of the examination region for scanning. With an infant, it is often necessary to secure the patient to the tabletop using a restraint or the like to comfortably and safely immobilize the infant to mitigate falling off the support and to reduce motion during scanning. However, a typical tabletop is configured to support adults, and, as such, the tabletop may not be well-suited to comfortably and safely immobilize an infant. An infant support, which horizontally slides partially onto the front end of the tabletop nearest the gantry, has been used to support an infant for scanning. Unfortunately, such a support may be difficult to install as there is limited space between the front end of the tabletop and the gantry, and, unlike positioning the infant directly on the tabletop, using such a support limits the region of the tabletop which can be used to scan an infant.

In view of at least the above, there is an unresolved need for other approaches that facilitates scanning an infant.

SUMMARY OF THE INVENTION

Aspects of the present application address the above-referenced matters and others.

According to one aspect, a subject support accessory includes a securing mechanism configured to secure to a tabletop of the subject support anywhere along a long axis of the tabletop by lowering the securing mechanism onto the tabletop.

According to another aspect, a method includes receiving, via slots in pivoting arms of an accessory, a tabletop, wherein the accessory is vertically lowered onto the subject support and the slots physically engage the tabletop. The method further includes releasably locking the arms, in response to receiving a force, so that the arms no longer pivot, thereby securing the subject support accessory to the subject support.

According to another aspect, a method includes securing an infant in an infant cradle, prepping the infant for an imaging procedure while the infant is secured in the infant cradle, and transporting the infant to an imaging examination room via the infant cradle. The method further includes securing the infant cradle, with the infant in the infant cradle, to a table top of an imaging support of an imaging system in the imaging examination room, wherein the infant table is configured to releasably lock to the table top by vertically lowering the infant cradle onto the table top until slots in pivoting arms of the infant cradle physically engage the table top and then applying a force that causes the arms to releasably lock in place.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
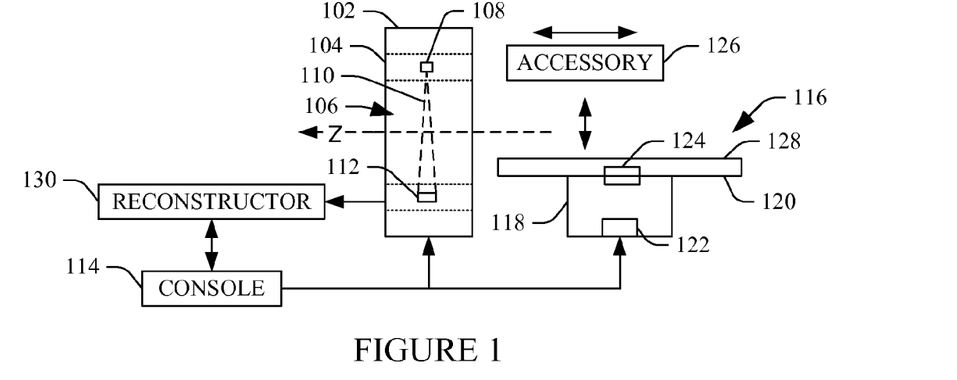
FIG. 1 schematically illustrates an imaging system in connection with a subject support and a subject support accessory.

FIG. 1 schematically illustrates an imaging system 100 such as a computed tomography (CT) scanner. In other embodiments, the imagines system 100 can include a positron emission tomography (PET) scanner, a single photon emission computed tomography (SPECT) scanner, a magnetic resonance (MR) scanner, and/or other imaging scanner. The illustrated imaging system 100 includes a stationary gantry 102 and a rotating gantry 104, which is rotatably supported by the stationary gantry 102. The rotating gantry 104 is configured to rotate around an examination region 106 about a longitudinal or z-axis.

A radiation source 108, such as an x-ray tube, is supported by and rotates with the rotating gantry 104 around the examination region 106. The radiation source 108 emits radiation that is collimated to produce a generally fan, wedge, cone, or otherwise shaped radiation beam 110 that traverses the examination region 106. A radiation sensitive detector array 112 includes a one or two dimensional array of detector pixels that respectively detect radiation that traverses the examination region 106 and generates an electrical signal indicative of the detected radiation.

A subject support 116, such as a patient couch, supports a human subject in the examination region 106. The subject support 116 includes a base portion 118 and a tabletop 120. The base portion 118 is affixed to or rests on the floor in the examination room and is configured to move vertically down and up for patient loading and unloading and for positioning the patient at a suitable height for scanning. A vertical drive system 122 includes a controller that drives a motor that drives the mechanism that raises and lowers the base 118.

The tabletop 120 is moveably affixed to the base portion 118 and is configured to move horizontally in and out of the examination region 106 before, during and after scanning. A horizontal drive system 124 includes a controller that drives a motor that drives a shaft attached to the tabletop 120 which moves the tabletop horizontally. In one instance, the motor is coupled to one end of the shaft, via a coupler, and the other end of the shaft is coupled to the tabletop via a yoke bridge of the like. In this instance, the horizontal controller drives the motor, which turns the coupler and hence the shaft, which, in turn, horizontally translates the tabletop 120.

A subject support accessory 126 is configured to affix to the tabletop 120. As described in greater detail below, in one instance, the accessory 126 is configured to releasably mount via a top side or surface 128 of the tabletop 120, vertically from a position above the tabletop 120, by lowering the accessory 126 onto the tabletop 120. Such an approach mitigates space constraints due to spacing between the gantries 102 and 104 and the subject support 116, such as those which may exist when attaching accessories configured to be mounted to the tabletop 120 horizontally along the z-axis to the front or back end of the tabletop 120.

Furthermore, with such an approach, placement of the accessory 126 is not limited on the tabletop 120 along the z-axis as with accessories that horizontally attach to the ends of the tabletop 120. As such, the user can place the accessory 126 anywhere on the tabletop 120, from the middle to a position where the accessory 126 extends beyond the tabletop 120. Where the accessory 126 extends as such into the examination region 106 and the tabletop 120 is not positioned in the path of the radiation beam during a scan, dose may be reduced relative to a scan where the beam also has to traverses the tabletop 120, which attenuates the radiation.

A reconstructor 130 reconstructs the signal generated by the detector array 112 and generates volumetric image data indicative of the examination region 106. A general purpose computing system serves as an operator console 114, and includes an output device such as a display, an input device such as a keyboard, mouse, and/or the like, one or more processor and computer readable storage medium. The console 114 allows the operator to control operation of the system 100, for example, selecting scan protocols, initiating scanning, etc.

Figure 2:
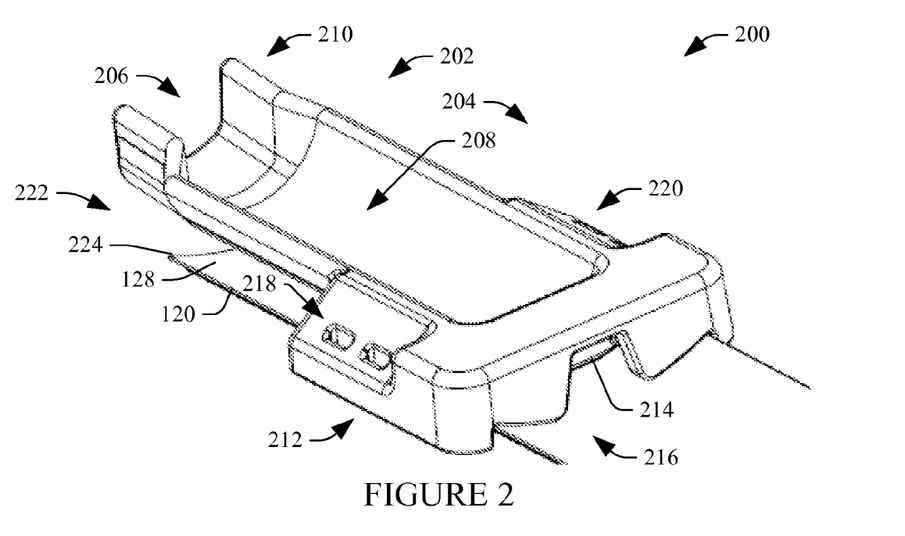
FIG. 2 schematically illustrates an example of an infant cradle subject support accessory.

FIG. 2 schematically illustrates a non-limiting example of the accessory 126. In this embodiment, the accessory 126 is an infant cradle 200. In other embodiments, the accessory 126 can be a head rest, a foot rest, an arm rest, an instrument holder, and/or other accessory.

The infant cradle 200 includes a first end region 202 and a second end region 204. An infant support portion 206 extends along the first and second end regions 202 and 204. The illustrated infant support portion 206 is semi-circular in shape and includes an infant receiving region 208 inside the semi-circle that is configured to receive an infant. At the first end region 202, the infant support portion 206 includes a head support 210.

A securing mechanism (not visible in FIG. 2, but shown and discussed in connection with FIGS. 3-9) is affixed to an underside 212 of the cradle 200 (or the side of the cradle 200 that faces the tabletop 120) in connection with the second end region 204 and is configured to releasably secure the infant cradle 200 to the tabletop 120. A release mechanism 214 is accessible from a rear portion 216 of the cradle 200. The release mechanism 214 releases a secured securing mechanism from the tabletop 120 and thus releases the cradle 200 from the tabletop 120.

The second end region 204 also includes slots 218 and 220 which are located on opposite sides of the support portion 206 across the infant receiving region 208 from each other. The slots 218 and 220 can be used to affix restraints (not shown) to the cradle 200 to secure an infant in the cradle 200. For example, a restraint can be fed through one of the slots 218 (or 220), across an infant in the support portion 206, and through the other of the slots 220 (or 218), and the ends of the restraints can secured.

Generally, the material of the cradle 200 has x-ray attenuation properties suitable for performing a diagnostic quality scans of an infant. An example of a suitable material includes, but is not limited to, HDPE HD 8760 series, which is a high density polyethylene resin produced by Exxon Mobil, a corporation of West Trenton, N.J., USA. Generally, this material may attenuate radiation to a lesser degree than the material of the tabletop 120. Other materials with similar and/or different properties are also contemplated herein.

With such a material, affixing the cradle 200 to the tabletop 120 such that it cantilevers or extends over the end of the tabletop 120 (as shown at 222 where the head rest portion 210 of the tabletop 120 extends beyond an end 224 of the tabletop 120), and scanning an infant with only the head rest portion 210 in the examination region 106 (FIG. 1) may allow for reducing patient dose relative to scanning the infant lying on the tabletop 120 (which attenuates radiation to a greater degree than the cradle 200) or both the cradle 200 and the tabletop 120 in the examination region 106.

Figure 3:
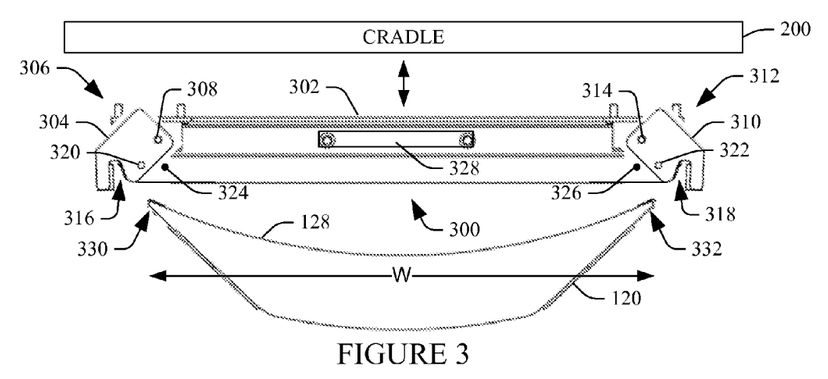
FIGS. 3, 4 and 5 schematically illustrate an example securing mechanism that can be employed with the subject support accessory to secure the subject support accessory to the subject support.
Figure 4:
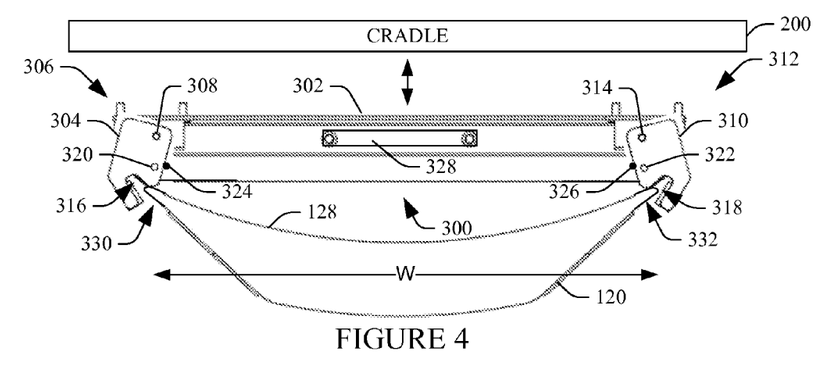
Figure 5:
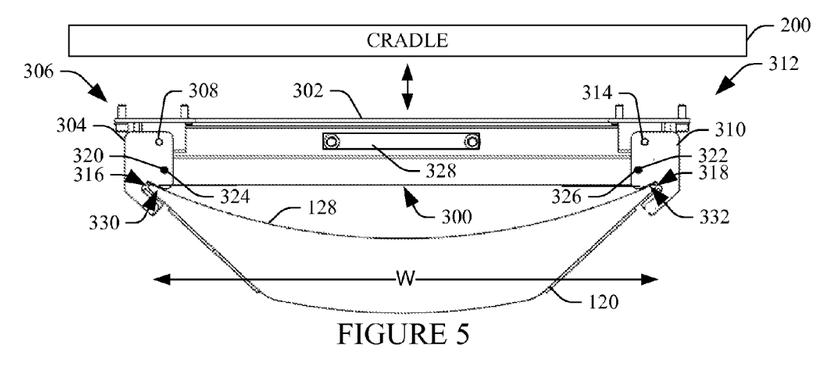

FIGS. 3, 4 and 5 schematically illustrate an example securing mechanism 300, which can be used with the cradle 200 and/or other accessory 126 to secure the cradle 200 and/or other accessory 126 to the tabletop 120. The securing mechanism 300 is shown disconnected from the cradle 200 in FIGS. 3-5 for sake of explanation. An example connection of the securing mechanism 300 to the cradle 200 is shown and discussed in connection with FIG. 10 herein.

The securing mechanism 300 includes elongate structural support 302, which spans along a width W of the tabletop 120. A first arm 304 is pivotably attached to a first end region 306 of the support 302 via a first pivot 308, and a second arm 310 is pivotably attached to a second opposing end region 312 of the support 302 via a second pivot 314. Ends of the arms 304 and 310 include slots 316 and 318 structurally configured to receive portions 330 and 332 of the tabletop 120. In this example, the arms 304 and 310 are pre-loaded such that the arms 304 and 310 tend to pivot away from each other about the pivots 308 and 314 as shown in FIG. 3.

The arms 304 and 310 also include material free regions such as holes 320 and 322, which are utilized to facilitate securing the support 302 and hence the cradle 200 to the tabletop 120. The support 302 also includes protrusions such as locking pins 324 and 326 configured to extend and retract through the holes 320 and 322 for locking and unlocking the support 302 to and from the tabletop 120. The release mechanism 214 includes a release bar 328 configured to facilitate retracting the pins 324 and 326 from the holes 320 and 322 to facilitate unlocking the support 302 from the tabletop 120 after the support 302 is secured to the tabletop 120.

In use, as the accessory 126 and hence the support 302 is lowered vertically onto the tabletop 120 and the arms 304 and 310 remain in the positions shown in FIG. 3, where the arms 304 and 310 pivot away from each other. As the slots 316 and 318 come into physical contact with the portions 330 and 332 of the tabletop 120, the contact causes the arms 304 and 310 to pivot towards each other as the portions 330 and 332 slide into the slots 316 and 318. When the arms 304 and 310 physically contact the pins 324 and 326, as shown in FIG. 4, the installer applies an additional force on the cradle 200 to cause the arms 304 and 310 to push the pins 324 and 326 back, allowing the arms 304 and 310 to pivot further.

Once the arms 304 and 310 pivot such that the holes 320 and 322 align with the pins 324 and 326, the force on the ends of the pins 324 and 326 is removed, and the pins 324 and 326 extend forward, into the holes 320 and 322, as shown in FIG. 5, securing the support to the tabletop 120. When the pins 324 and 326 are in the holes 320 and 322, the arms 304 and 310 are inhibited from pivoting, and the support 302 is secured to the tabletop 120, securing the accessory 126 at a static location on the tabletop 120 such that the accessory 126 will not move. As such, the securing mechanism 300 can be considered self-latching.

For unlocking the accessory 126 from the tabletop 120, the release mechanism 214 is actuated to retract the pins 324 and 326 from the holes 320 and 322, allowing the arms 304 and 310 to pivot away from each other so that the arms 304 and 310 can pivot back to the location shown in FIG. 4. The arms 304 and 310 freely pivot back to this position, under their pre-loading, when there is no other force applied to the accessory sufficient to inhibit such pivoting. When unlocked, the accessory 126 can be removed from the tabletop 120 (via vertically lifting the accessory 126 off the tabletop 120).

FIGS. 6, 7, 8 and 9 schematically illustrate an example configuration of a suitable release mechanism 214 in connection with the pin 324. A similar or other configuration can be used for the locking pin 326. Note that the relative sizes and/or the positions of the components in these figures are provided for explanatory purposes and is not limiting. Other release mechanisms are also contemplated herein.

In these figures, the locking pin 324 is attached to a member 602, which is pulled forward, in a direction towards the support 302, via a pre-loaded spring 604. The spring 604 is loaded such that the member 602 moves the pin 324 forward when no force is applied to the end of the pin 324 and allows the pin 324 to move away from the support 302 when a sufficient force is applied to the end of the pin 324.

Figure 6:
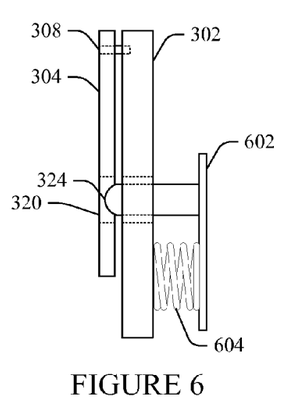
FIGS. 6, 7, 8 and 9 schematically illustrate an example locking mechanism that can be utilized with the securing mechanism to lock the subject support accessory to the subject support.
Figure 7:
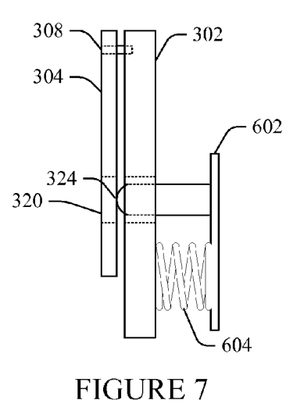

In FIG. 6, the arm 304 is in a position away from the pin 324 and the member 602 pulls the pin 324 forward. Note that when no force is applied to the pin 324, the pre-loaded spring 604 causes the pin 324 to extend out into the plane in which the arm 304 pivots. In FIG. 7, the arm 304 pivots and physically contacts the pin 324, exerting a force on the pin 324 that is sufficient to move the pin 324 behind the plane in which the arm 304 pivots against the pre-load exerted by the spring 604.

Figure 8:
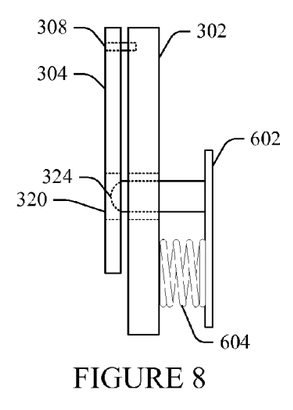
Figure 9:
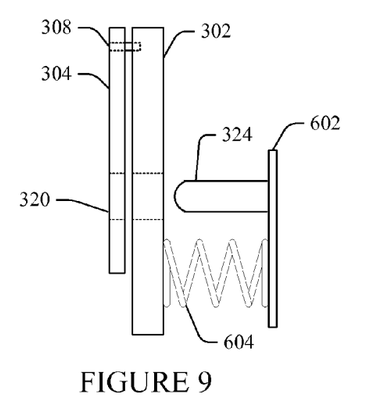

In FIG. 8, the hole 320 in the arm 304 aligns with the pin 324, and the member 602 moves the pin 324 into the hole 320 of the arm 304 and into the plane in which the arm 304 pivots. With the pin 324 in this position, the arm 304 is inhibited from pivoting. In FIG. 9, the release bar 328 is used to move the member 602 away from the support 302, causing the pin 324 to move out of the hole 320 and allowing the arm 304 to pivot, even though the hole 320 is aligned with the pin 324.

Figure 10:
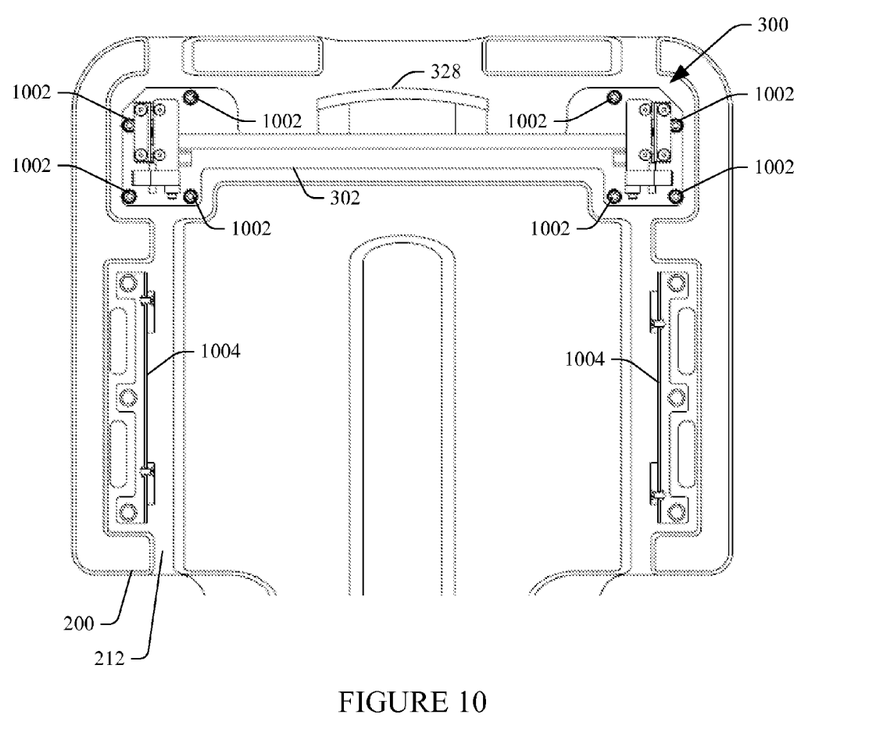
FIG. 10 schematically illustrates an example approach for coupling the securing mechanism to the subject support accessory.

FIG. 10 schematically illustrate an example coupling between the securing mechanism 300 and the underside 212 of the cradle 200.

In this example, the support 302 is fastened to the cradle via fasteners 1002 such as screws, rivets, snaps, or the like. Where the fasteners 1002 can be readily connected and unconnected by a user (e.g., snaps), the securing mechanism 300 can be interchangeably used with a plurality of different accessories 126 for the subject support 116 and/or different securing mechanisms can be used with the same accessory 126 (e.g. the cradle) so that one accessory 126 can be used with multiple imaging modalities and/or different tabletops.

In this example, rails 1004 are also fastened to the cradle 200. The rails 1004 may be part of the securing mechanism 300 or separate therefrom. The rails 1004 are pivotably mounted to the cradle 200 so as to pivot in the same direction as the arms 304 and 310. The pivotable attachment allows the rails 1004 to pivot and conform to the mechanical tolerance differences between tabletops 120. In one instance, this allows the accessory 126 to be self-aligning along the z-axis on the tabletop 120. The rails 1004, when resting on the tabletop 120, provide further support for the cradle 200.

Figure 11:
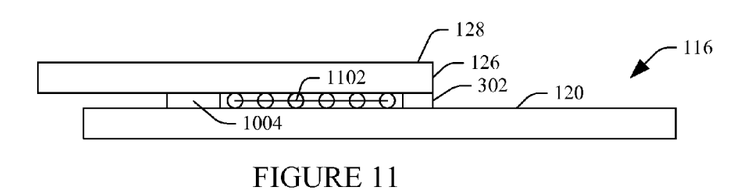
FIGS. 11, 12, 13 and 14 schematically illustrate example non-limiting variations of the subject support accessory in connection with the subject support.

FIG. 11 illustrates an embodiment in which the accessory 126 includes wheels 1102, which facilitate moving the accessory 126 along the tabletop 120. In FIG. 11, the wheels 1102 are located between the support 302 and the rails 1004. In other embodiments, the wheels 1102 may be otherwise located. The wheels 1102 are configured such that when the support 302 is not locked to the tabletop 120, the accessory 126 can roll, under operator control, along the tabletop 120. However, when the support 302 is locked to the tabletop 120, the accessory 126 cannot be rolled.

Figure 12:
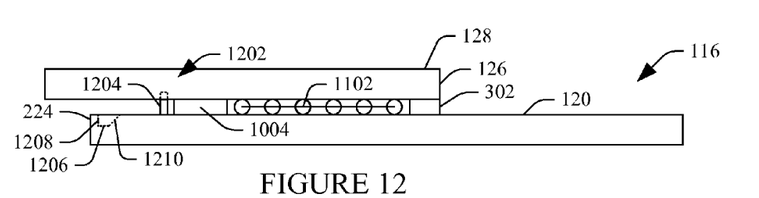
Figure 13:
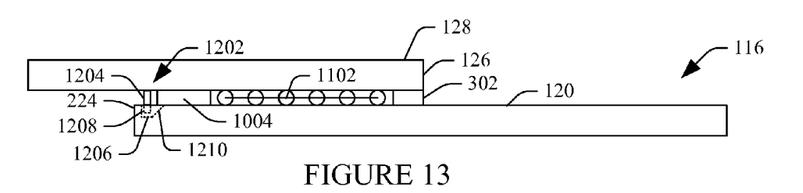

FIGS. 12 and 13 illustrate an embodiment substantially similar to FIG. 11, with the addition of a mechanism 1202 which limits the amount of the accessory 126 that can cantilever over the end of the tabletop 120. The mechanism 1202 includes a pin 1204, which is slidably affixed in the accessory 126. The mechanism 1202 further includes a complementary slot 1206 in the tabletop 120. The slot 1206 includes a first side 1208 which extends generally perpendicular from the top of the tabletop 120 into the tabletop 120, and a second side 1210 which extends at angle from the top of the tabletop 120 into the tabletop 120.

FIG. 12 shows the mechanism 1202 when the pin 1204 is not in the slot 1206, and FIG. 13 shows the mechanism 1202 when the pin 1204 is in the slot 1206. When the pin 1204 is not in the slot 1206, the accessary 126 can be rolled in either direction along the tabletop 120. However, when the pin 1204 is in the slot 1206, the accessary 126 is prevented from being advanced any further along the tabletop 120 in the direction of the end 224 of the tabletop 120, but allowed to move in the opposite direction, where the pin 1204 slides up the second side 1210, partially into the accessory 126, and out of the slot 1206.

Figure 14:
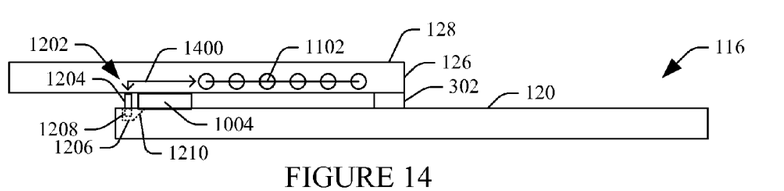

FIG. 14 illustrates an embodiment substantially similar to FIGS. 12 and 13, with the addition that when the pin 1204 enters the slot 1206, a mechanism 1400 causes the wheels 1102 to retract into the accessory 126, either fully (as shown) or partially, such that the wheels 1202 no longer physical contact the tabletop 120. With this configuration, when the pin 1204 is removed from the slot 1206 (e.g., as described in connection with FIGS. 12 and 13), the mechanism 1400 causes the wheels 1102 to again physically contact the tabletop 120.

Figure 15:
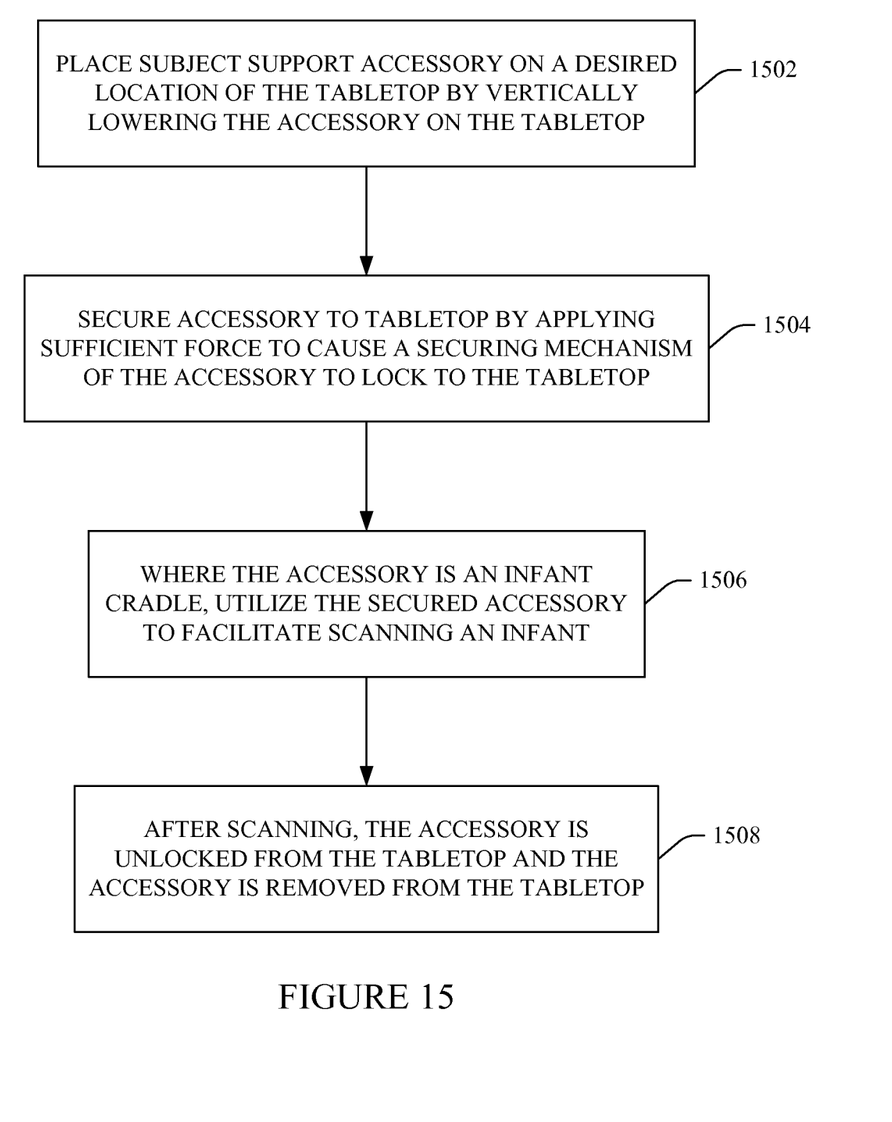
FIG. 15 schematically illustrates an example method.

FIG. 15 illustrates a method in accordance with the above.

It is to be appreciated that the ordering of the acts in the methods described herein is not limiting. As such, other orderings are contemplated herein. In addition, one or more acts may be omitted and/or one or more additional acts may be included.

At 1502, a subject support accessory is placed at a desired location on the tabletop. As described herein, the accessory can be placed essentially anywhere along the tabletop, using a vertical mounting approach in which the accessory is lowered vertically down onto the tabletop.

At 1504, the accessory is secured to the tabletop be exerting sufficient force on the tabletop, which causes a securing mechanism of the accessory to engage and lock to the tabletop.

At 1506, where the accessory is an infant cradle, an infant can be scanned using the accessory. As discussed herein, where the infant cradle 200 is mounts so as to cantilever over the end of the subject support, patient dose may be reduced.

At 1508, after scanning the infant, the accessory can be unlocked from the tabletop and vertically removed therefrom and/or moved to a different location on the tabletop.

It is to be appreciated that the infant can be placed in the infant cradle 200 before the cradle 200 is installed on the tabletop. This allows for preparing the infant for the scan outside the imaging exam room, if desired, and/or using the cradle 200 as a transportation device.

Additionally or alternatively, the infant cradle 200 can be removed from the tabletop before the infant is removed from the cradle 200. This allows for removing the infant from the infant cradle 200 outside of the imaging exam room, if desired, and/or using the cradle 200 as a transportation device.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A subject support accessory for a subject support of an imaging system, comprising:
   a securing mechanism configured to secure the subject support accessory to a tabletop of the subject support in a fixed position relative to a top surface of the tabletop anywhere along a long axis of the tabletop by lowering the securing mechanism onto the tabletop, and wherein the securing mechanism comprises pivot arms, each pivot arm with a slot which engages surfaces of the tabletop in the fixed position; and
   a locking mechanism that locks the securing mechanism to the tabletop with force applied vertically toward the top surface of the tabletop, wherein the locking mechanism comprises: a hole in each arm; and a locking pin in the support, wherein the locking pin slides into the hole in response to the arm pivoting and aligning the hole with the pin, thereby inhibiting the arm from pivoting.

2. The subject support accessory of claim 1, further including:
   an accessory which is fastened to the securing mechanism and the accessory includes an infant cradle, and a vertical force is applied to the accessory to lock the subject support accessory in position.

3. The subject support accessory of claim 1, wherein the slots in the pivot arms of the securing mechanism engage lateral surfaces of the tabletop to secure the subject support accessory to the tabletop.

4. The subject support accessory of claim 3, wherein the securing mechanism, further comprising:
   a support fastened to an accessory, wherein each pivot arm is pivotably affixed to the support, and pivots towards to the tabletop, engaging the tabletop, in response to lowering the securing mechanism onto the tabletop and physically contacting the tabletop.

5. The subject support accessory of claim 1, wherein the locking pin is slidable between a first position in which the pin is outside of a pivot plane of the arm and a second position in which the pin is in the pivot plane.

6. The subject support accessory of claim 5, wherein the arm urges the locking pin from the second position to the first position in response to the arm physically contacting the locking pin.

7. The subject support accessory of claim 1, wherein the locking mechanism further comprises:
   a member, wherein the locking pin is mounted to the member; and
   a pre-loaded spring which pulls the member towards support, thereby moving the locking pin towards the pivot plane.

8. The subject support accessory of claim 7, wherein the locking mechanism further comprises:
   a release mechanism connected to the securing mechanism which releases the locking pin from the hole.

9. The subject support accessory of claim 8, wherein the release mechanism urges the member away from the support, thereby moving the locking pin away from the pivot plane.

10. The subject support accessory of claim 1, wherein the securing mechanism is configured to releasably affix alternatively to the accessory and at least one other accessory.

11. The subject support accessory of claim 1, further comprising,
    a pin extending in a vertical direction toward the top surface of the tabletop, which when extended into a slot of the top surface of the tabletop, prevents an unsecured accessory in contact with the top surface of the tabletop from moving in a direction of a front end of the tabletop.

12. The subject support accessory of claim 1, further comprising,
    an accessory which includes a side and at least one wheel disposed between the side and the top surface of the tabletop, which facilitates moving the accessory horizontally along the top surface of the tabletop.

13. A method of securing a subject support accessory to a subject support of an imaging system, comprising:
    receiving the tabletop via slots in pivoting arms of a securing mechanism fastened to the accessory wherein the securing mechanism fastened to the accessory is vertically lowered onto the subject support and the slots physically engage the tabletop;
    releasably locking the pivoting arms, in response to receiving a vertical force applied to the subject support accessory, so that the pivoting arms no longer pivot, thereby securing the subject support accessory to the subject support in a fixed position relative to the top surface of the tabletop; and
    unlocking the arms, thereby allowing the arms to pivot toward a pre-loaded position, wherein the accessory is vertically raised away from the tabletop, the arms pivot, and the slots disengage from the tabletop.

14. The method of claim 13, wherein releasably locking the arms includes sliding a locking pin into a hole of the arm.

15. The method of claim 14, wherein the locking pin is urged into the hole via a pre-loaded spring.

16. The method of claim 13, wherein unlocking the arms includes sliding the locking pin out of the hole of the arm.

17. The method of claim 13, wherein the slots are configured to engage portions of a surface of the tabletop anywhere along a longitudinal axis of the tabletop.

18. The method of claim 13, wherein the accessory includes an infant cradle.

* * * * *